US009863963B2

(12) United States Patent
Poppe et al.

(10) Patent No.: US 9,863,963 B2
(45) Date of Patent: Jan. 9, 2018

(54) METHOD AND REAGENT FOR DETERMINING VITAMIN D METABOLITES

(71) Applicant: ORGENTEC DIAGNOSTIKA GMBH, Mainz (DE)

(72) Inventors: Robert Poppe, Mainz (DE); Vukic Soskic, Mainz (DE)

(73) Assignee: ORGENTEC DIAGNOSTIKA GMBH, Mainz (DE)

( * ) Notice: Subject to any disclaimer, the term of this patent is extended or adjusted under 35 U.S.C. 154(b) by 135 days.

(21) Appl. No.: 14/778,796

(22) PCT Filed: Mar. 19, 2014

(86) PCT No.: PCT/EP2014/055503
§ 371 (c)(1),
(2) Date: Sep. 21, 2015

(87) PCT Pub. No.: WO2014/147121
PCT Pub. Date: Sep. 25, 2014

(65) Prior Publication Data
US 2016/0047825 A1 Feb. 18, 2016

(30) Foreign Application Priority Data
Mar. 21, 2013 (DE) .................. 10 2013 205 055

(51) Int. Cl.
G01N 33/82 (2006.01)
(52) U.S. Cl.
CPC .................. G01N 33/82 (2013.01)
(58) Field of Classification Search
CPC .................................. G01N 33/82
See application file for complete search history.

(56) References Cited

U.S. PATENT DOCUMENTS 7,087,395 B1   8/2006 Garrity et al.
7,964,363 B2   6/2011 Armbruster et al.
(Continued)

FOREIGN PATENT DOCUMENTS

CN    101273272 A    9/2008
CN    101467048 A    6/2009
(Continued)

OTHER PUBLICATIONS

English Translation of Chinese Office Action dated Aug. 29, 2016 issued in corresponding CN 201480017334.8 application (7 pages).
(Continued)

Primary Examiner — Krishnan S Menon
Assistant Examiner — Dwan A Gerido
(74) Attorney, Agent, or Firm — Millen White Zelano and Branigan, PC; Csaba Henter; John Sopp

(57) ABSTRACT

The present invention relates to a method for releasing bound vitamin D by bringing a sample containing vitamin D into contact with a release reagent which contains at least one hydrotropic substance and at least one transition metal salt. The released vitamin D can subsequently be determined quantitatively. The present invention relates further to a reagent for releasing and optionally determining vitamin D, containing at least one hydrotropic substance and at least one transition metal salt, as well as to the use of such a release reagent for releasing and optionally determining vitamin D.

22 Claims, 2 Drawing Sheets

(56) References Cited

U.S. PATENT DOCUMENTS

| | | |
|---|---|---|
| 8,003,400 B2 | 8/2011 | Kobold et al. |
| 9,341,552 B2 | 5/2016 | Kyriatsoulis et al. |
| 2004/0096900 A1 | 5/2004 | Laurie et al. |
| 2009/0093445 A1 | 4/2009 | Kyriatsoulis et al. |
| 2010/0068725 A1* | 3/2010 | Armbruster ............ G01N 33/82 435/7.1 |
| 2010/0285603 A1 | 11/2010 | Kobold et al. |
| 2013/0078729 A1 | 3/2013 | Antoni et al. |
| 2015/0024506 A1 | 1/2015 | Antoni et al. |
| 2015/0104876 A1 | 4/2015 | Kyriatsoulis et al. |
| 2015/0226753 A1 | 8/2015 | Antoni et al. |

FOREIGN PATENT DOCUMENTS

| | | |
|---|---|---|
| CN | 102906570 A | 1/2013 |
| DE | 102006017315 A1 | 10/2007 |
| DE | 102007005942 A1 | 8/2008 |
| EP | 2126586 B1 | 6/2010 |
| WO | 02/057797 A2 | 7/2002 |
| WO | 2007118748 A1 | 10/2007 |
| WO | 2008092519 A1 | 8/2008 |
| WO | 2008092917 A1 | 8/2008 |
| WO | 2008/138783 A1 | 11/2008 |
| WO | 2011/144661 A1 | 11/2011 |

OTHER PUBLICATIONS

English Abstract of CN 101273272 A published Sep. 24, 2008.
English Abstract of CN 101467048 A published Jun. 24, 2009.
English Abstract of CN 102906570 A published Jan. 30, 2013.
German Search Report dated Mar. 21, 2013 issued in corresponding DE 10 2013 205 055.0 application (pp. 1-5).
International Search Report dated Jul. 4, 2014 issued in corresponding PCT/EP2014/055503 application (pp. 1-6).
Database WPI, Thomson Scientific, XP002726076, (Feb. 2011) pp. 1-2.
"Iron (III) p-toluenesulfonate", Internet Citation, XP00792273, (Aug. 2005) pp. 1-5.
B.K Roy, et al., "Functions of hydrotropes (sodium salicylate, proline, pyrogallol, resorcinol and urea) in solution with special reference to amphiphile behaviors", Colloids and Surfaces A: Physicochemical and Engineering Aspects, vol. 203, No. 1-3 (Apr. 2002) pp. 155-166.
A. M. Saleh, et al., "Study of the interaction of menadione with hydrotropic salts", DIE Pharmazie, vol. 29, No. 8 (Aug. 1974) pp. 525-527.
W. Franken, et al., "Analytical evaluation of a new automated protein binding assay to determine 25-hydroxyvitamin D concentrations", Clin Chem Lab Med, vol. 50, No. 11 (2012) pp. 2037-2039.

* cited by examiner

METHOD AND REAGENT FOR DETERMINING VITAMIN D METABOLITES

The present invention relates to a method for releasing bound vitamin D by bringing a sample containing vitamin D into contact with a release reagent which contains at least one hydrotropic substance and at least one transition metal salt. The released vitamin D can subsequently be determined quantitatively. The present invention relates further to a reagent for releasing and optionally determining vitamin D, containing at least one hydrotropic substance and at least one transition metal salt, as well as to the use of such a release reagent for releasing and optionally determining vitamin D.

For humans, adequate provision with vitamin D is essential. The most frequent physiological forms of vitamin D are vitamin D3 or vitamin D2. The most important physiologically active derivatives of vitamin D3 (cholecalciferol) are 25OHD3 (25-hydroxy vitamin D3 or calcidiol) and 1,25-(OH)$_2$ D3 (1-alpha, 25-dihydroxy vitamin D3 or calcitriol). Generally, most vitamin D3 is not absorbed with food like other vitamins but is produced in the skin under the influence of UV light. Here, 7-dihydroxycholesterol is converted by UV irradiation into previtamin D3, the unstable intermediate being reorganised into vitamin D3. In food, vitamin D3 is contained especially in oily fish. A further form of vitamin D which can occur in the body is vitamin D2 (calciferol or ergocalciferol), which occurs in fungi and can be absorbed with food. Vitamin D3 and vitamin D2 preparations represent a further source for provision with a sufficient amount of vitamin D.

Vitamin D and its natural derivatives are extremely hydrophobic molecules. In the blood, vitamin D is transported in a complex with vitamin D-binding protein (DBP). DBP belongs to the family of the albumins and binds vitamin D, vitamin D metabolites and fatty acids.

In the liver, vitamin D is oxidised by cytochrome P450 at position C-25. The resulting 25OHD (25-hydroxy vitamin D3 or 25-hydroxy vitamin D2) is the vitamin D metabolite mainly present in the circulation. The concentration of 25OHD in serum serves as an indicator for evaluating the vitamin D status of humans.

In the kidneys and in other tissues, 25OHD is converted to 1,25(OH)$_2$D, the physiologically active form of vitamin D, which, after binding to the vitamin D receptor (VDR), controls vitamin D-dependent regulated (VDRE) gene activities.

Adequate provision of vitamin D is important for normal bone structure and for regulating calcium and phosphate resorption. Activation of VDR with 1,25(OH)$_2$D increases the efficiency of intestinal calcium uptake by about 30% and phosphate uptake by about 80%. If the serum concentration of 25OHD falls below 30 ng/ml, this is associated with a significant reduction in calcium resorption in the intestine and an increase in parathyroid hormone concentration. Vitamin D deficiency is an important factor for osteoporosis with an increased risk of bone fracture and is associated with further health risks. While the concentration of vitamin D in serum is subject to considerable variations depending on food intake and exposure to the sun, the 25OHD serum concentration is a good indicator for determining the vitamin D provision status. The 25OHD concentration in serum is therefore routinely determined in medical diagnostics.

The binding of 25OHD and other vitamin D substances to DBP represents a major hurdle in determining vitamin D metabolites. All methods of determination require the vitamin D metabolite to be released from the DBP complex.

In order to be able to determine vitamin D and its metabolites in serum, they must be released from binding with DBP. This can be carried out by various methods, such as, for example, precipitating DBP with organic solvents (for example ethanol, methanol) or extracting vitamin D and its metabolites from the aqueous phase using phase-forming solvents, such as, for example, chloroform or hexane.

U.S. Pat. No. 7,482,162 B2 (Immunodiagnostic Systems Ltd.) describes the use of 8-anilino-1-naphthalenesulfonic acid ammonium salt (8-ANS) as a non-competitive displacement reagent for releasing 1,25(OH)2D bound to DBP.

WO 2011/144661 (Roche Diagnostics GmbH) describes a reagent mixture which contains carbonate- or hydrogen carbonate-releasing substances in combination with reducing agents and alkalinising substances, wherein the release of vitamin D metabolites from the DBP complex takes place in the pH range 11-14.

EP 2 126 586 (Immundiagnostik AG) relates to the use of a proteolytic method using proteinase K for inactivating the DBP of the resulting release of vitamin D metabolites and the subsequent determination of vitamin D metabolites in an ELISA test system.

U.S. Pat. No. 7,087,395 (Quest) relates to a method for releasing vitamin D metabolites from DBP by pretreating the serum at pH 13 with an alkaline reagent mixture consisting of NaOH, detergents, cyclodextrin derivatives and salicylic acid salts.

WO 2008/138783 (Nordic Biosciences A/S) describes the pretreatment of a serum or plasma sample with pamoic acid in order to release vitamin D from the DBP complex.

However, methods hitherto known for releasing vitamin D from the complex with DBP are either labour-intensive and difficult to automate or susceptible to faults.

Automatable test methods for determining vitamin D require the vitamin D to be released from the complex with DBP under conditions which ideally permit direct further analysis of the reaction mixture. However, DBP is a very stable protein and is present in a relatively high serum concentration, which corresponds to a binding capacity of 1900 ng/ml for vitamin D. With an average 25OHD serum concentration of 30 ng/ml, this represents a 60-fold excess of binding capacity for 25OHD.

A release reagent should accordingly detach vitamin D from the stable bond with DBP, inactivate the considerable excess of vitamin D binding capacity that is present owing to the high DBP serum concentration, and additionally allow the released vitamin D to be bound to a detection reagent, generally an antibody.

Accordingly, it is an object of the present invention to provide a reagent for releasing bound vitamin D which solves the current problems associated with the release of bound vitamin D from protein complexes and is suitable for use in an automated method for the direct quantitative determination of vitamin D.

The limitations and disadvantages of the reagent compositions of the prior art are eliminated at least in part by the present invention. The present invention provides a reagent for releasing bound vitamin D which permits efficient release of vitamin D. This reagent can additionally contain a determination reagent for vitamin D. The use of the release reagent offers the advantage that the vitamin D to be determined does not have to be isolated from the sample. The sample with the added release reagent can be subjected directly to an immunological determination method without additional treatment. This allows vitamin D to be determined in a manner that is less expensive and less time-consuming than is known in the prior art.

By means of the present invention there is accordingly provided a reliable and automatable method for determining the concentration of vitamin D, in particular of 25-hydroxy vitamin D3 or 25-hydroxy vitamin D2.

A first aspect of the present invention relates, therefore, to an in vitro method for releasing vitamin D, comprising the steps of:
a) bringing a sample that contains vitamin D, in particular in the form of complexes with proteins, into contact with a release reagent comprising:
   i. at least one hydrotropic substance, and
   ii. at least one transition metal salt, and
b) releasing the bound vitamin D.

Unless otherwise indicated, the expression "vitamin D" includes all naturally occurring compounds which have the vitamin D2 basic structure or the vitamin D3 basic structure according to the structural formulae I or II.

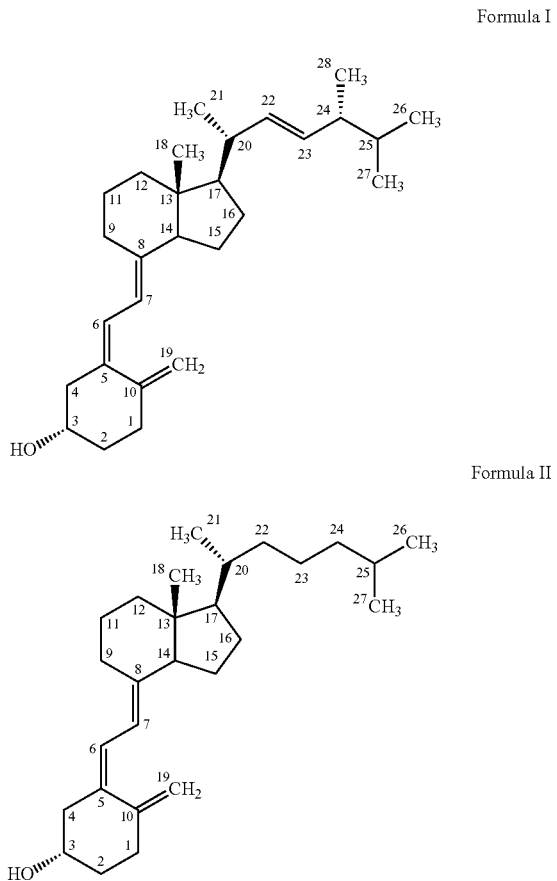

Formula I

Formula II

The numbering of the carbon atoms in the structural formulae I and II is given in accordance with steroid nomenclature. 25-hydroxy vitamin D denotes vitamin D metabolites which are hydroxylated at position 25 of the structural formula I or II, that is to say 25-hydroxy vitamin D2 and 25-hydroxy vitamin D3. Further hydroxy vitamin D compounds are, for example, 1,25-dihydroxy vitamin D or 24,25-dihydroxy vitamin D.

1,25-dihydroxy vitamin D refers to the active forms of vitamin D (the so-called D hormones), which are hydroxylated at position 1 as well as at position 25 of the structural formulae I and II.

Other well known vitamin D compounds are 24,25-dihydroxy vitamin D2, 24,25-dihydroxy vitamin D3 and C3-epi-25-hydroxy vitamin D.

The expression "releasing bound vitamin D" means the complete or partial separation of vitamin D from complexes with proteins, in particular DBP, to which it is bound. Preferably, substantially all of the vitamin D present in the sample is released. In this connection, "substantially" means that at least 90%, 95%, 98% and preferably at least 99% of the vitamin D is released.

The expression "hydrotropic substance" or "hydrotropic compound" denotes compounds which increase the solubility of insoluble or sparingly soluble organic compounds in aqueous media. In the process, the hydrotropic compounds reduce the surface tension of the water and thus facilitate the dispersion of the substances that are to be dissolved (hydrotropy).

The expression "transition metal salt" denotes inorganic or organic salts of metals of groups III-XII or of groups Ib-VIIb and VIII of the periodic table of elements.

The sample to be tested is preferably a biological fluid selected, for example, from blood, serum, plasma or milk. The sample is usually from a living being, preferably from a mammal, for example from a human.

The hydrotropic substance is preferably an aromatic acid and/or an ester, amide or salt thereof. It is preferably selected from the group consisting of N,N-dimethylbenzamide, dimethylbenzoic acid, 1,2-naphthoquinonesulfonic acid, para-toluenesulfonic acid, sulfanilic acid, anthraquinone-2-sulfonic acid, aniline-2-sulfonic acid and/or salts thereof. The hydrotropic substance is particularly preferably toluenesulfonic acid and/or an ester, amide or salt thereof.

The hydrotropic substance further preferably has an HLB value of from 12 to 18. The expression "HLB value" (hydrophilic lipophilic balance) is a measure, introduced by W. C. Griffin, of the hydrophilicity and lipophilicity of non-ionic surfactants and emulsifiers. The corresponding HLB value of a compound can be determined by methods known in the specialist field.

The transition metal salts of the method according to the invention preferably include salts of the metals of groups 5, 6, 7, 8, 10 and/or 12, for example salts of vanadium, chromium, manganese, iron, cobalt, nickel and/or zinc. The transition metal salt is particularly preferably an iron(III) salt and most preferably iron(III) chloride or iron(III) citrate. The salts consist of transition metal cations and inorganic or organic anions.

The inorganic anions include halides, such as, for example, fluoride, chloride, bromide or iodide, sulfide, carbonate, hydrogen carbonate, sulfate, phosphate, nitrate and rhodanide.

The organic anions include carboxylic acid anions, such as, for example, formate, acetate, palmitate, citrate, oxalate, fumarate, benzoate, maleate or salicylate, and organic sulfates, such as, for example, lauryl sulfate.

The release reagent can further contain a complexing agent, preferably citrate, EDTA and/or a salt thereof, most preferably citrate and/or a salt thereof. The expression "complexing agent" denotes compounds which are capable of forming complexes, such as, for example, chelating agents.

The release reagent is added to the sample preferably in an amount to give a final concentration of from 200 to 1000 mM, in particular from 300 to 700 mM, of the hydrotropic substance and a final concentration of from 5 to 100 mM, in particular from 10 to 40 mM, of the transition metal salt. The release reagent is preferably placed as a stock solution in an aqueous medium which has from 5 to 30 wt. %, preferably from 10 to 25 wt. %, of the hydrotropic substance and from 0.1 to 5 wt. %, preferably from 0.2 to 2 wt. %, of the transition metal salt, based on the total weight of the release reagent.

A further aspect of the present invention comprises an in vitro method for determining vitamin D compounds, comprising the steps of:
a) bringing a sample that contains bound vitamin D, in particular in the form of complexes with proteins, into contact with a release reagent comprising:
  i. at least one hydrotropic substance, and
  ii. at least one transition metal salt,
b) releasing the bound vitamin D, and
c) determining the released vitamin D.

The determination of the released vitamin D according to step c) can be carried out after steps a) and b) or together with steps a) and b) in terms of time. Step c) is preferably performed at the same time as steps a) and b) without separating the release reagent from the vitamin D to be determined, whereby a one-step method for determining vitamin D in a sample is provided.

The determination of the concentration of vitamin D in step c) is preferably an immunological method in which the vitamin D to be determined binds to an immunological binding partner to form an immune complex. The expression "immunological binding partner" includes antibodies.

Examples of suitable immunological methods include heterogeneous assays, homogeneous assays, sandwich assays, competition assays, enzyme immunoassays, radioimmunoassays, fluorescence polarisation immunoassays, microparticle enzyme immunoassays and chemoluminescent magnetic immunoassays. Many of the test formats described above can be carried out either as a one-step method or as a two-step method. Tests formats that can be carried out as a one-step method are preferably used.

The expression "heterogeneous assay" refers to methods in which the immune complex must be separated from other constituents, for example by washing.

The expression "homogeneous assay" refers to methods in which the immune complex does not have to be separated from the other constituents.

The expression "competition assay" refers to methods in which the vitamin D present in the sample competes with a detectable (for example labelled) tracer for an immunological binding partner.

The expression "sandwich assay" refers to methods in which vitamin D is bound between two immunological binding partners, at least one of which is detectable (for example by labelling).

The expression "enzyme immunoassay" refers to methods which use an enzyme as label. Examples of such labels are alkaline phosphatase, horseradish peroxidase and β-galactosidase. ELISA (enzyme-linked immunosorbent assay) is, for example, a preferred heterogeneous sandwich enzyme immunoassay.

The term "radioimmunoassay" refers to methods which use a radioactive isotope as label. An example of such a label is iodine 125.

The suitable methods comprise a detection step. This can comprise label detection. Any labels known in this field for such purposes can be used. Examples of suitable labels include enzyme labels (as described above), radioisotope labels (as described above), fluorescent labels, such as, for example, fluorescein or rhodamine, chemoluminescent labels, such as, for example, luminol or acridinium ester, and polyhistidine labels.

A competitive immunological method is particularly preferably used for determining the concentration of vitamin D in step c). Suitable competitive test formats are well known to the person skilled in the art. In a typical competitive binding assay, a receptor or antibody having a tracer, that is to say a labelled form of vitamin D, is brought into contact with the sample to be tested. The amount of tracer which is found bound to the receptor or antibody is indicative of the proportion of unlabelled vitamin D in the sample. Alternatively, a competitive binding assay can comprise bringing a receptor or antibody bound to a tracer into contact with the sample to be tested and measuring the amount of displaced tracer, which is indicative of the amount of vitamin D in the sample. A tracer labelled with biotin and detection by means of peroxidase-labelled streptavidin are most preferably used.

Preferably, no sample constituents are separated off for determining the vitamin D. Method steps a), b) and c) can be carried out in a single reaction vessel without extraction or purification being carried out between the individual method steps.

The vitamin D released and to be determined by means of the method according to the invention includes all known vitamin D compounds, for example 25-hydroxy vitamin D3, 25-hydroxy vitamin D2, 1,25-dihydroxy vitamin D3, 1,25-dihydroxy vitamin D2, vitamin D3, vitamin D2 and mixtures thereof. The vitamin D compounds are particularly preferably 25-hydroxy vitamin D3 and/or 25-hydroxy vitamin D2.

A further aspect of the present invention relates to a reagent for releasing vitamin D, comprising:
a) at least one hydrotropic substance, and
b) at least one transition metal salt.

The reagent preferably further contains a complexing agent. Citrate, EDTA and/or a salt thereof are preferably used as the complexing agent, more preferably citrate and/or a salt thereof.

In a further embodiment, the reagent further comprises at least one reagent for determining vitamin D.

A further aspect of the present invention is the use of the above-described reagent for releasing bound vitamin D and optionally for determining the released vitamin D.

BRIEF DESCRIPTION OF DRAWINGS

The present invention will be described in greater detail below by means of the following drawings and examples.
Legend to the Figures.

D2 concentrations and the direct 25-OH vitamin D3/D2 determination method using the automatic Alegria™ system (ORG270, ORGENTEC).

EXAMPLE 1: PREPARATION OF A VITAMIN D RELEASE REAGENT

Sodium toluenesulfonate was dissolved in water and adjusted with stock solutions of 1 M sodium citrate and 1 M iron(III) chloride to a final concentration of 1 M sodium toluenesulfonate, 100 mM sodium citrate and 50 mM iron (III) chloride.

EXAMPLE 2: BINDING OF A 25-OHD ANTIBODY TO A SOLID PHASE

An antibody against 25-OH-vitamin D3 or 25-OH-vitamin D2 was diluted in tris-buffered saline pH 8.0 to a concentration of 1 µg/ml. The wells of a microtitre plate (Maxisorb, Nunc) were coated with 100 µl of the diluted antibody, dried at 37° C. and stored at 4° C. until the test was carried out.

EXAMPLE 3: COMPETITIVE BINDING ANALYSIS

Figure 1:
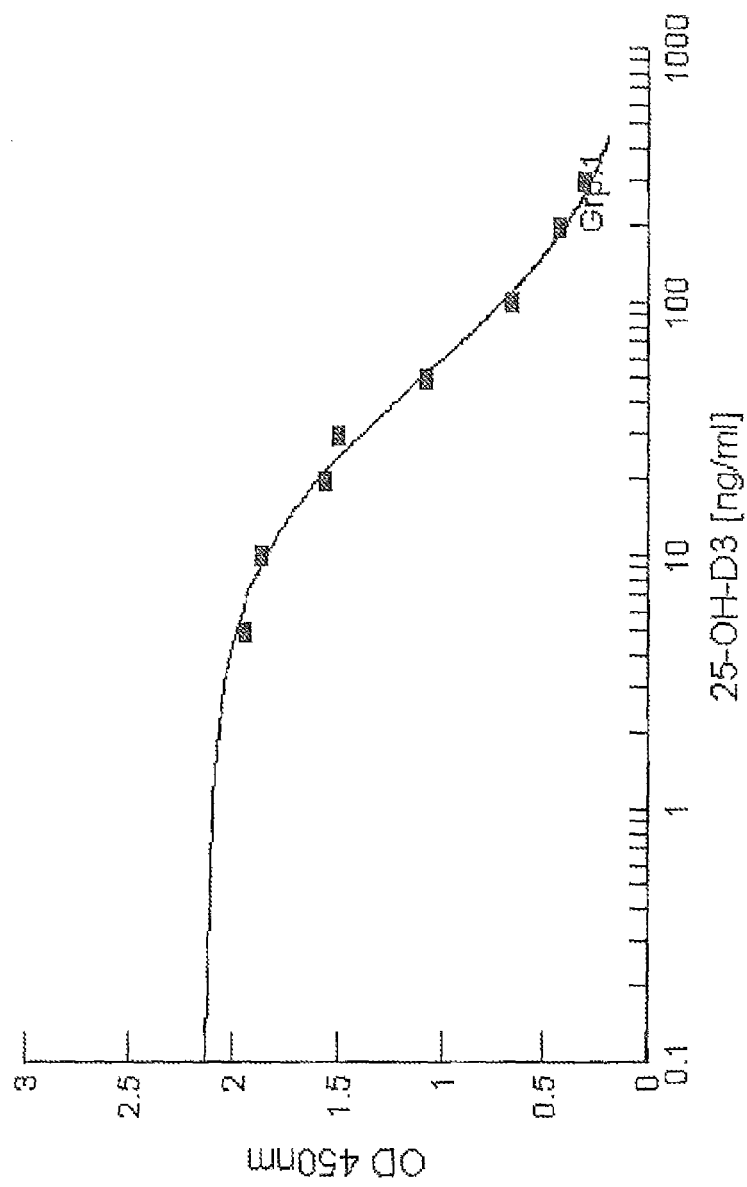
FIG. 1: Characterisation of the release of defined 25OHD3 concentrations from binding with serum DBP and competition with biotin-25OHD3 tracer reagent. For the ELISA detection of the specific 25OHD competition, 80 µl of vitamin D release reagent were added to serial dilutions of 25OHD3 in vitamin D-free serum matrix (SerCon, Seracare Inc.) in concentrations of 0, 5, 10, 20, 20, 50, 100, 200, 300 ng/ml in the presence of 7.5 ng/ml of biotin-25OHD tracer reagent and applied to microtitre plate wells coated with an anti-25OHD antibody. The binding of the tracer on the basis of the competing 25OHD concentration was determined with peroxidase-labelled streptavidin and a tetramethylbenzidine (TMB) colour reaction by measuring the OD 450 nm.

Defined concentrations of 25-OHD3 were added to vitamin D-free serum matrix (Seracon, Seracare Inc.). In each case 80 µl of the concentration series were filled into a microtitre plate well pre-loaded with 25-OHD-biotin tracer and incubated for 5 minutes at RT (20-27° C.) for resolubilisation of the tracer reagent. 80 µl of the vitamin D release reagent from Example 1 were then added to the sample and mixed. 100 µl of the samples diluted with vitamin D release reagent were transferred into wells coated with 25OHD antibody and incubated for 30 minutes at room temperature. The sample batch was then removed and the wells were rinsed 3× with 200 µl of wash buffer each time. The antibody-bound biotin-25OHD tracer was detected with peroxidase-labelled streptavidin and a tetramethylbenzidine (TMB) colour reaction. After the substrate reaction had been stopped by addition of 100 µl of 50 mM phosphoric acid, the optical density was measured at 450 nm. A specific competition of the biotin-25OHD tracer was demonstrated here, as shown in FIG. 1, even at a 25OHD3 concentration of 5 ng/ml.

EXAMPLE 4: DETERMINATION OF 25-HYDROXY VITAMIN D IN SERUM OR PLASMA IN THE AUTOMATIC ALEGRIA™ 25-OH VITAMIN D3/D2 TEST SYSTEM

In order to study the correlation between HPLC+LC-MS/MS based 25OHD3/D2 determination methods and the automatic Alegria™ 25-OH vitamin D3/D2 test system, serum or plasma samples the 25OHD3/D2 concentration of which was characterised by HPLC+LC-MS/MS based methods (6PLUS1 Multilevel Serum Calibrator Set 25-OH-vitamin D3/D2, Chromsystems GmbH) and dilution stages thereof were stored in aliquots at −20° C. until the determination.

For determination in the automatic Alegria™ 25-OH vitamin D3/D2 test system, in each case 80 µl of the samples were placed in well A of the Alegria™ test strip. The 8 wells of a test strip contained the vitamin D release reagent, streptavidin-HRP conjugate, TMB substrate, a 25OHD calibrator solution and 25-OHD antibody-coated wells for in each case one sample determination. Test processing took place automatically in the Alegria™ machine. Inside a test strip, the sample and the calibrator, which was internal to the test strip, were mixed with 25OHD-biotin tracer and vitamin D release reagent, transferred to the 25OHD antibody-coated wells and washed after being incubated for 30 minutes. The antibody-bound biotin-25OHD tracer was detected with peroxidase-labelled streptavidin and a tetramethylbenzidine (TMB) colour reaction by measuring the optical density at 650 nm.

Figure 2:
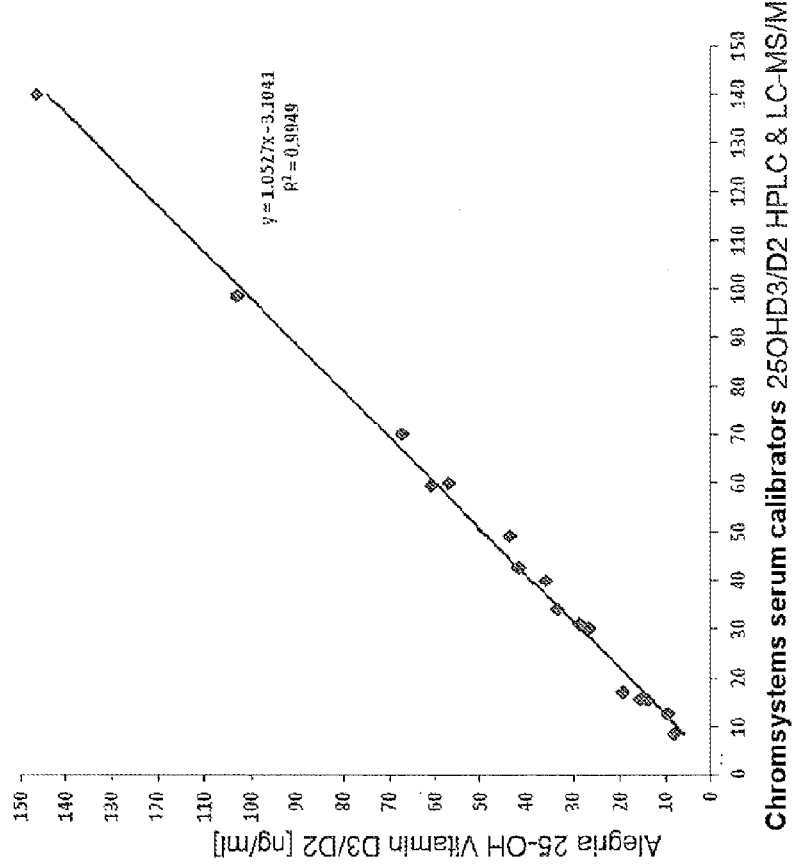
FIG. 2: The comparative analysis of serums with defined 25OHD3 and 25OHD2 concentrations (6PLUS1 Multilevel Serum Calibrator Set 25-OH-vitamin D3/D2, Chromsystems GmbH) and dilutions thereof in vitamin D-free serum matrix (SerCon, Seracare Inc.) showed a high correspondence between the HPLC and LC-MS/MS defined 25OHD3/

As is shown in FIG. 2, a high correspondence was observed between the HPLC and LC-MS/MS defined 25-OHD3/D2 concentrations in serum samples and the direct 25-OH vitamin D3/D2 determination method in the automatic Alegria™ system (ORG270, ORGENTEC).

The invention claimed is:

1. A reagent for determining vitamin D, comprising:
   i) a vitamin D-releasing agent comprising:
      a) at least one hydrotropic substance,
      b) at least one transition metal salt, and
      c) optionally at least one complexing agent,
   wherein the vitamin D-releasing reagent has from 5 to 30 wt. % of the at least one hydrotropic substance and from 0.1 to 5 wt. % of the at least one transition metal salt, based on the total weight of the reagent, in an aqueous fluid; and
   (ii) a determination reagent for vitamin D.

2. The reagent according to claim 1, wherein the hydrotropic substance is an aromatic acid and/or an ester, amide or salt thereof.

3. The reagent according to claim 1, wherein the transition metal salt is the salt of a metal of group 5, 6, 7, 8, 10 and/or 12.

4. The reagent of claim 1, wherein the vitamin D-releasing reagent has from 10 to 25 wt. % of the at least one hydrotropic substance and from 0.2 to 2 wt. %, of the at least one transition metal salt, based on the total weight of the reagent, in an aqueous fluid.

5. The reagent according to claim 1, wherein the hydrotropic substance is N,N-dimethylbenzamide, dimethylbenzoic acid, 1,2-naphthoquinonesulfonic acid, para-toluenesulfonic acid, sulfanilic acid, anthraquinone-2-sulfonic acid, aniline-2-sulfonic acid and/or a salt thereof.

6. The reagent according to claim 1, wherein the hydrotropic substance is toluenesulfonic acid and/or an ester, amide or salt thereof.

7. The reagent according to claim 1, wherein the transition metal salt is a salt of vanadium, chromium, manganese, iron, cobalt, nickel and/or zinc.

8. The reagent according to claim 1, wherein the transition metal salt is an iron(III) salt.

9. The reagent according to claim 1, wherein the transition metal salt is iron(III) chloride or iron(III) citrate.

10. The reagent according to claim 1, further comprising a labelled form of vitamin D as a tracer.

11. The reagent according claim 1, wherein the determination reagent for vitamin D comprises an immunological binding partner for vitamin D.

12. The reagent according to claim 11, wherein the immunological binding partner for vitamin D is a receptor or an antibody for vitamin D.

13. An in vitro method for releasing vitamin D by a reagent according to claim 1, comprising the steps of:
   a) bringing a sample that contains bound vitamin D into contact with the vitamin D-releasing agent, and
   b) releasing the bound vitamin D.

14. The method according to claim 13, wherein the sample is a biological fluid which is blood, serum, plasma or milk.

15. The method according to claim 13, wherein the hydrotropic substance is an aromatic acid and/or an ester, amide or salt thereof.

16. The method according to claim 13, wherein the transition metal salt is the salt of a metal of group 5, 6, 7, 8, 10 and/or 12.

17. The method according to claim 13, wherein the release reagent further contains a complexing agent.

18. The method according to claim 13, wherein the release reagent is added to the sample in an amount to give a final concentration of from 200 to 1000 mM of the hydrotropic substance and/or a final concentration of from 5 to 100 mM of the transition metal salt.

19. The method according to claim 13, wherein the vitamin D is 25-hydroxy vitamin D3, 25-hydroxy vitamin D2, 1,25-dihydroxy vitamin D3, 1,25-dihydroxy vitamin D2, vitamin D3, vitamin D2 or a mixture thereof.

20. An in vitro method for determining vitamin D by a reagent according to claim 1, comprising the steps of:
    a) bringing a sample that contains bound vitamin D into contact with the vitamin D-releasing agent,
    b) releasing the bound vitamin D, and
    c) determining the released vitamin D.

21. The method according to claim 20, wherein vitamin D is determined without separating off the release reagent.

22. The method according to claim 20, wherein the concentration of vitamin D is determined in step c) by an immunological method.

\* \* \* \* \*